US 9,234,514 B2

(12) United States Patent
Jones (10) Patent No.: US 9,234,514 B2
(45) Date of Patent: Jan. 12, 2016

(54) TWO-CHAMBER BLOOD PUMP

(75) Inventor: Kenneth A. Jones, McKinney, TX (US)

(73) Assignee: QUEST MEDICAL, INC., Allen, TX (US)

(*) Notice: Subject to any disclaimer, the term of this patent is extended or adjusted under 35 U.S.C. 154(b) by 449 days.

(21) Appl. No.: 12/199,593

(22) Filed: Aug. 27, 2008

(65) Prior Publication Data

US 2009/0060756 A1    Mar. 5, 2009

Related U.S. Application Data

(60) Provisional application No. 60/968,220, filed on Aug. 27, 2007.

(51) Int. Cl.
| | |
|---|---|
| *F04B 1/02* | (2006.01) |
| *A61M 1/00* | (2006.01) |
| *F04B 9/04* | (2006.01) |
| *F04B 43/02* | (2006.01) |
| *A61M 1/10* | (2006.01) |
| *F04B 7/00* | (2006.01) |
| *F04B 23/06* | (2006.01) |
| *F04B 53/14* | (2006.01) |

(52) U.S. Cl.
CPC .............. *F04B 43/02* (2013.01); *A61M 1/1046* (2013.01); *A61M 1/1081* (2013.01); *A61M 1/1086* (2013.01); *F04B 7/00* (2013.01); *F04B 23/06* (2013.01); *F04B 43/026* (2013.01); *F04B 53/14* (2013.01); *A61M 2202/047* (2013.01); *A61M 2205/12* (2013.01)

(58) Field of Classification Search
CPC . A61M 1/1046; A61M 2205/12; F04B 23/06; F04B 43/02; F04B 53/14; F04B 7/00
USPC .............. 417/3, 4, 42, 43, 44.2, 63, 244, 254, 417/265; 92/98 R, 98 D, 99, 136; 604/151–153
See application file for complete search history.

(56) References Cited

U.S. PATENT DOCUMENTS

| | | | |
|---|---|---|---|
| 3,955,557 A | | 5/1976 | Takagi |
| 4,116,589 A | | 9/1978 | Rishton |
| 4,236,880 A | * | 12/1980 | Archibald ...................... 417/478 |
| 4,391,600 A | * | 7/1983 | Archibald ...................... 604/153 |
| 4,397,617 A | | 8/1983 | Sergio et al. |
| 4,410,322 A | * | 10/1983 | Archibald ...................... 604/153 |
| 4,611,578 A | | 9/1986 | Heimes |

(Continued)

*Primary Examiner* — Peter J Bertheaud
*Assistant Examiner* — Dominick L Plakkoottam
(74) *Attorney, Agent, or Firm* — David W. Carstens; Sudhakar V. Allada; Carstens & Cahoon, LLP (57) ABSTRACT

A fluid pump for medical applications. The pump includes a flexible cassette containing two pump chambers of differing volume, each chamber having a dedicated piston. The first piston pushes fluid from the first chamber to the second, and the second piston pushes fluid from the second chamber and out of the pump. Three valves are coordinated with the action of the pistons to control fluid flow into and out of the pump chambers by applying and releasing pressure to and from specific points of the flexible cassette. A control system controls the operation of the pistons and valves and directs the pistons to be advanced according to a time-varying velocity profile. The first pump chamber passively fills and then rapidly expels the collected fluid into the second chamber at low pressure. The second chamber, once filled, expels the fluid downstream at high pressure, producing a pulsatile pressure profile.

9 Claims, 11 Drawing Sheets

(56) References Cited

U.S. PATENT DOCUMENTS

| | | | |
|---|---|---|---|
| 4,648,877 A | 3/1987 | Lundback | |
| 4,687,424 A | 8/1987 | Heimes | |
| 4,781,716 A | 11/1988 | Richelsoph | |
| 4,820,300 A | 4/1989 | Pierce et al. | |
| 4,936,759 A * | 6/1990 | Clausen et al. | 417/423.15 |
| 5,066,283 A | 11/1991 | Skrabal | |
| 5,300,015 A | 4/1994 | Runge | |
| 5,609,572 A * | 3/1997 | Lang | 604/22 |
| 5,638,737 A * | 6/1997 | Mattson et al. | 92/101 |
| 5,645,531 A * | 7/1997 | Thompson et al. | 604/67 |
| 5,688,245 A | 11/1997 | Runge | |
| 5,702,358 A | 12/1997 | Witherspoon et al. | |
| 6,110,410 A * | 8/2000 | Owens et al. | 264/491 |
| 6,454,697 B1 | 9/2002 | Wang | |
| 6,620,121 B1 | 9/2003 | McCotter | |
| 6,746,416 B2 | 6/2004 | Hubbard et al. | |
| 6,860,866 B1 | 3/2005 | Graf et al. | |
| 7,169,352 B1 | 1/2007 | Felt et al. | |
| 7,226,276 B2 * | 6/2007 | Bez et al. | 417/250 |
| 2004/0136835 A1 * | 7/2004 | Bez et al. | 417/254 |
| 2005/0234392 A1 * | 10/2005 | Mineshima et al. | 604/29 |

\* cited by examiner

TWO-CHAMBER BLOOD PUMP

CROSS-REFERENCE TO RELATED APPLICATIONS

This application claims the benefit of and priority to U.S. Provisional Patent Application No. 60/968,220 filed Aug. 27, 2007, the technical disclosures of which are hereby incorporated herein by reference.

TECHNICAL FIELD

The present invention relates to a piston assembly, and more specifically to a piston pump mechanism that delivers a sterile fluid for medical treatment.

BACKGROUND OF THE INVENTION

Extracorporeal blood pumps or in vivo heart assist devices comprise various designs, including peristaltic roller pump, centrifugal pumps, axial floe pumps, pneumatic chamber pumps, and hydraulic chamber pumps. These pumps vary widely in cost and efficacy, and their uses vary from supporting a patient on a heart/lung machine to assisting the human heart as a bridge to transplant or replacing the human heart.

Recent research suggests that better cardiac perfusion is obtained with a pulsatile flow than with a constant-rate flow since the heart is a reciprocating pump and delivers a pulsatile flow. A number of designs have been developed to introduce a pulsatile component to extracorporeal circulation. These designs generally fall into two categories. The first category consists of those devices that combine a roller or centrifugal pump with an additional device that periodically compresses the tube through which the blood or cardioplegia flows. Examples of these devices include U.S. Pat. No. 4,116,589 (RISHTON) Sep. 26, 1978, and U.S. Pat. No. 6,620,121 (MCCOTTER) Sep. 16, 2003.

A second category consists of devices in which the pump itself is used to produce a pulsatile flow. In one type of pump, such as that in U.S. Pat. No. 5,702,358, the number of revolutions per minute (RPM) of a centrifugal pump is varied in a periodic fashion to achieve a roughly pulsatile flow. In U.S. Pat. No. 5,300,015 (RUNGE) Apr. 5, 1994, a type of peristaltic pump is described, which achieves a pulsatile flow. Both of these types of designs, however, are limited in their ability to produce a pulsatile flow of desired characteristics while still maintaining a desired average flow rate.

Therefore there is a need for an apparatus for extracorporeal circulation that produces a significantly pulsatile flow, while still-maintaining a user-specified average flow rate.

SUMMARY OF THE INVENTION

The present invention provides a fluid pump for medical applications. The invention comprises a flexible cassette containing two pump chambers, wherein the first pump chamber is larger than the second pump chamber. The pump includes two pistons, one for each pump chamber. The first piston pushes fluid from the first chamber to the second, and the second piston pushes fluid from the second chamber downstream out of the pump. Three valves are coordinated with the action of the pistons to control fluid flow into and out of the pump chambers by applying and releasing pressure to and from specific points of the flexible cassette.

A control system controls the operation of the pistons and valves and directs the pistons to be advanced according to a time-varying velocity profile. The first pump chamber passively fills and then rapidly expels the collected fluid into the second chamber at low pressure. The second chamber, once filled, expels the fluid downstream at high pressure, producing a pulsatile pressure profile downstream.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of an illustrative embodiment when read in conjunction with the accompanying drawings, wherein:

DETAILED DESCRIPTION OF THE DRAWINGS

The present invention provides a piston/volumetric chambered blood pump that comprises of two chambers, two pistons, three valves and a flexible cassette. The invention mimics the function of half the human heart and may be used in any circulatory support application. The key element of the invention is the presence of two pump chambers within a sterile cassette that are acted upon by pistons and valves to allow filling and expulsion as required to serve the intended use.

Figure 1:
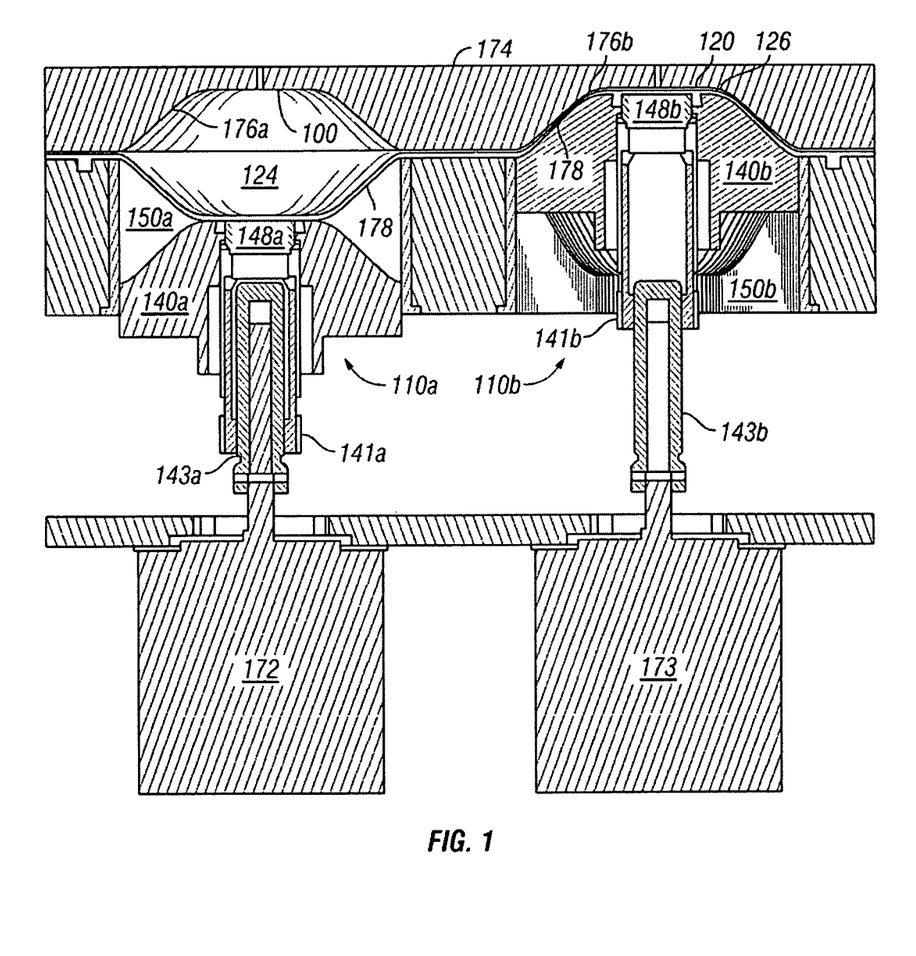
FIG. 1 is a schematic illustration of the functioning of one embodiment of a pump mechanism for use in a preferred embodiment of the present invention.

FIG. 1 illustrates one embodiment of a pump mechanism for incorporation into a fluid delivery system. The pump mechanism operates on a flexible, disposable fluid cassette 120 which maintains the sterility of the fluid as it passes through the mechanism. The pump mechanism 100, as described herein, features two piston assemblies 110a, 110b. The piston assembly 110 of the present invention enables the delivery of fluids at a definable, consistent volumetric flow rate. A fluid delivery system incorporating the present invention may have multiple applications within the medical industry and, in particular, applications in at least the areas of intravenous fluid delivery, limb perfusion, organ perfusion and cardioplegia delivery.

Notwithstanding the foregoing, the present invention is adaptable to be incorporated into any variety of fluid delivery systems, whether medical related or not, and scalable to provide a large range of volumetric flow rates.

Figure 2:
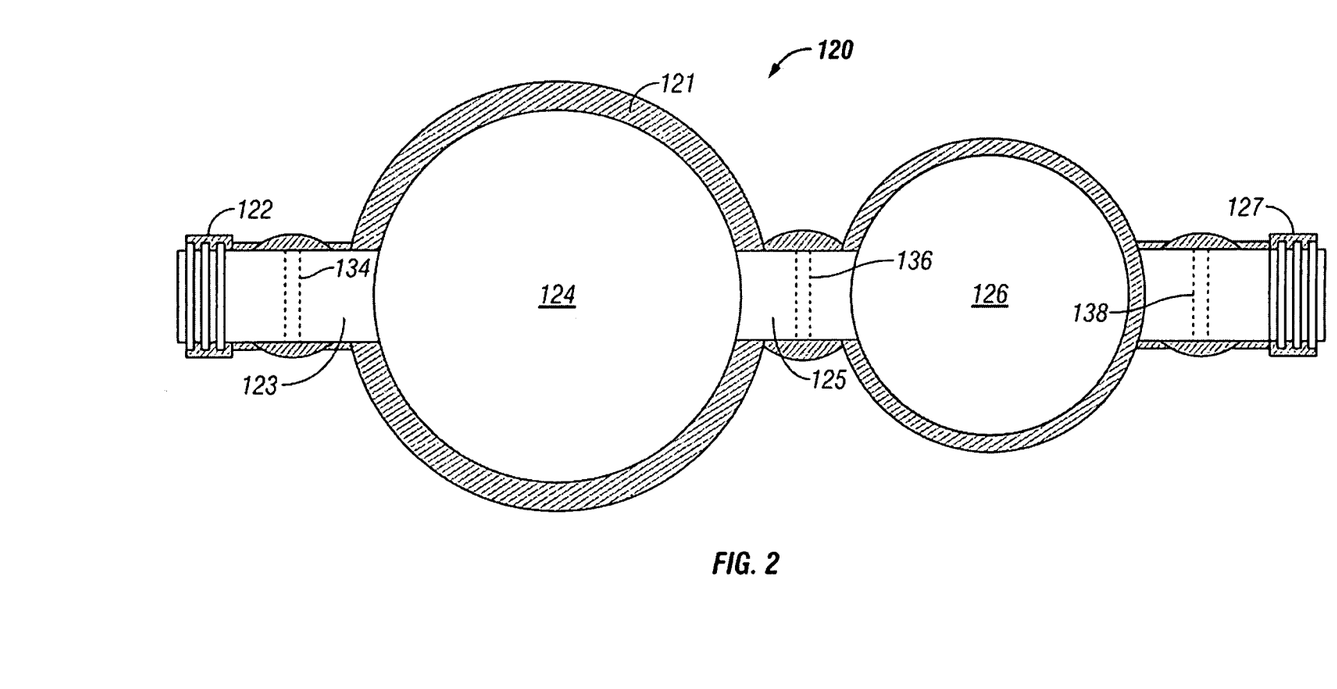
FIG. 2 is a plan view of one embodiment of a disposable fluid cassette for the pump mechanism of FIG. 1.

FIG. 2 illustrates a disposable fluid cassette in accordance with a preferred embodiment of the present invention. The cassette 120 may be formed from two thin, flexible sheets of material, such as polyvinylchloride. The sheets are bonded together along a selected bond area 121 to form particularized open flow paths and chambers. Any number of techniques (as an example, radio frequency (RF) welding) may be employed for such bonding. The thickness of the material should be such that variations which occur during manufacture should not significantly affect the volumetric accuracy of the fluid output of pump mechanism.

The cassette 120 includes a fluid inlet 122. A fluid entry path 123 runs from the inlet 122 to a first pump chamber 124. The first pump chamber 124 is proximal to a second chamber 126, connected by an inlet flow path 125. The outlet path 127 is the gateway for passage of the fluid to other portions of the fluid delivery system or directly to the patient.

Figure 3:
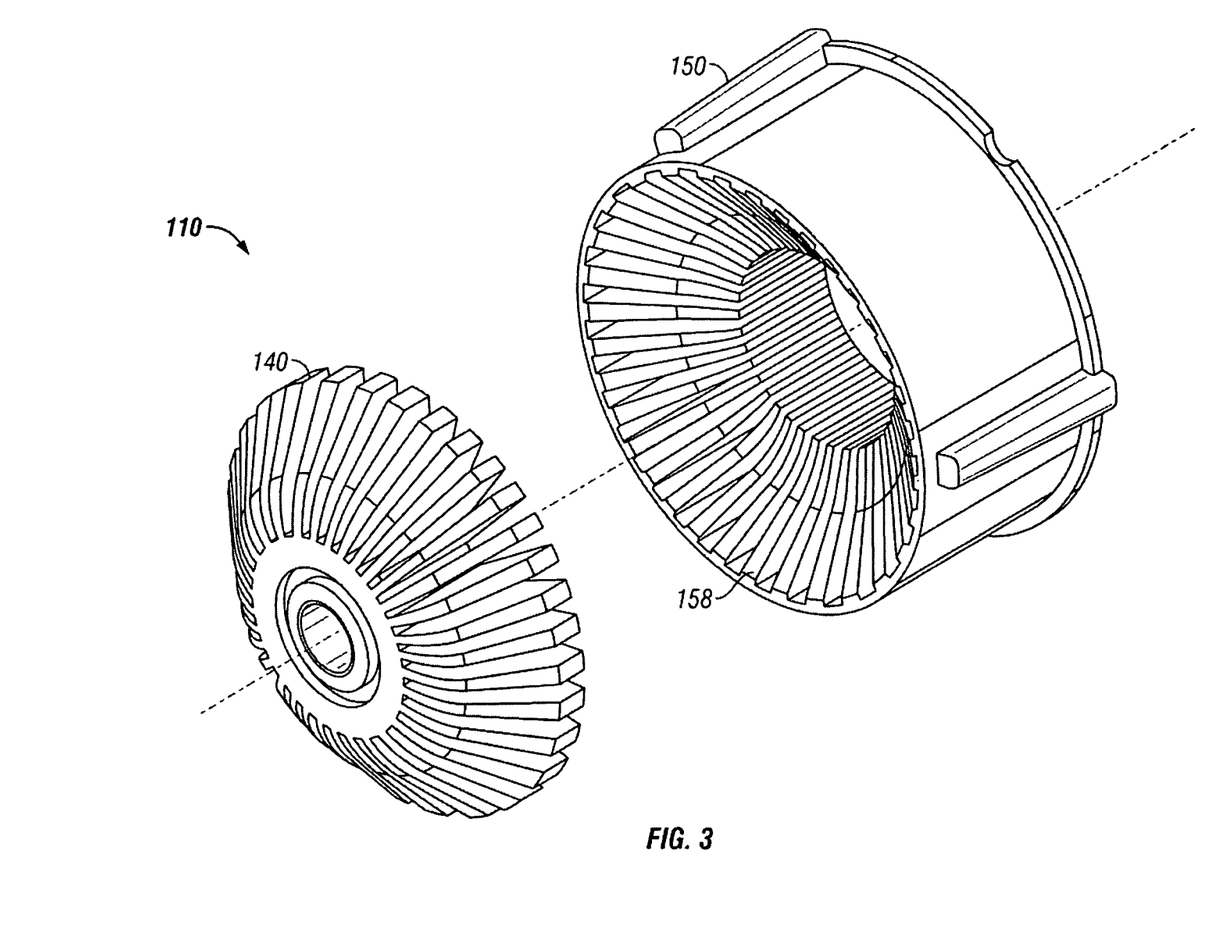
FIG. 3 is an exploded, perspective view of a piston assembly in accordance with a preferred embodiment of the present invention.
Figure 4:
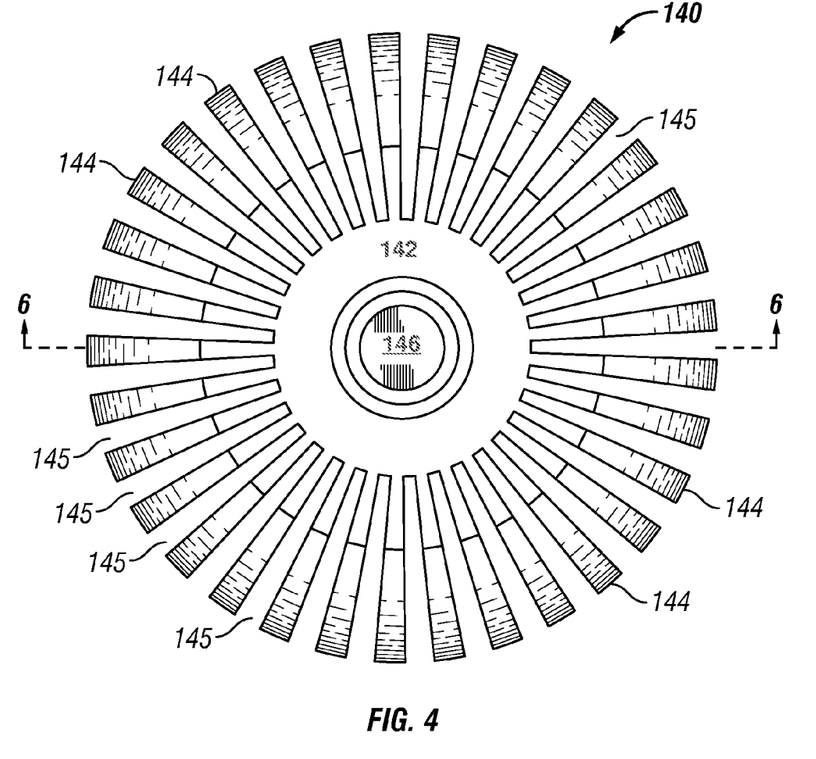
FIG. 4 is a plan view of the piston of the piston assembly of FIG. 3.
Figure 5:
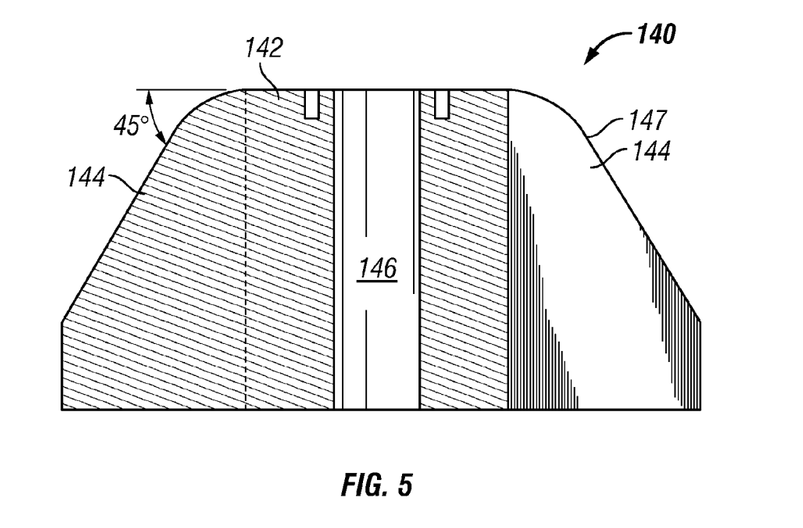
FIG. 5 is a sectional view of the piston along line 6-6 of FIG. 4.

FIG. 3 illustrates the piston assembly 110 of FIG. 1. The piston assembly 110 has a piston 140 and a base 150, such base 150 being dimensioned to operatively receiving the piston 140. As shown in FIGS. 4 and 5, piston 140 includes a central hub 142 with a plurality of splines 144 extending outwardly therefrom. The plurality of splines 144 are integrally formed with the hub 142 and extend radially outward. The piston 140 generally forms a convex supporting surface 147, wherein each spline 144 progresses from a full height at the hub 142 to a substantially lesser height at the perimeter of the piston 140. In the preferred embodiment, the angular displacement of the supporting surface 147 corresponds, although in a differing direction of displacement, to an angular displacement of a facial surface, or receiving surface 158, of the base 150.

Figure 9:
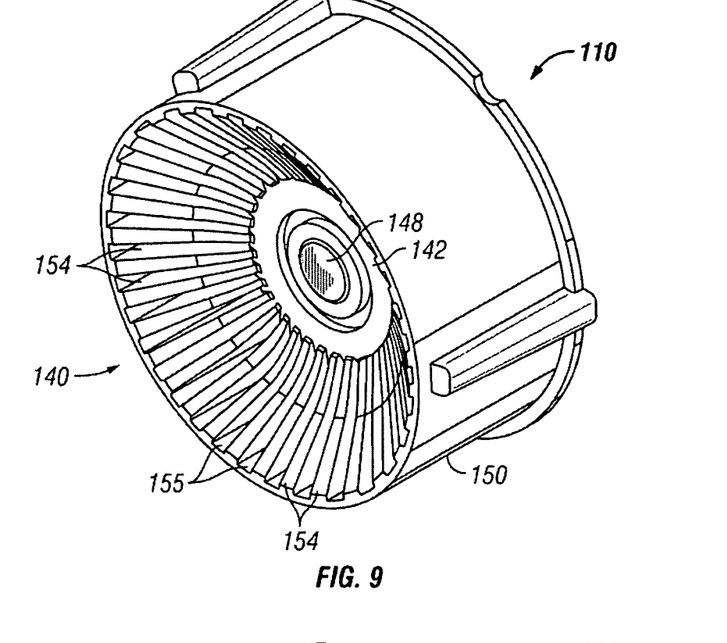
FIG. 9 is a perspective view of the piston assembly of FIG. 3 in a fully retracted state.

As shown in FIG. 4, the hub 142 can include a passage 146 extending through the piston 140, such passage 146 extending along an axial centerline of the piston 140. In the preferred embodiment, the passage 146 receives and carries a contact pressure sensor 148 (see FIGS. 9 and 10). The incorporation of a pressure sensor 148 in the piston 140 permits monitoring of a fluid pressure within a pumping chamber associated with piston 140. Consequently, the intrachamber fluid pressure is useful in determining:
1. The volumetric content of the pumping chamber,
2. The presence of non-occluding valves adjacent the pump chamber, and
3. The presence of excessive fluid delivery pressures as well as excessive back-pressures presented to pump mechanism.

Figure 6:
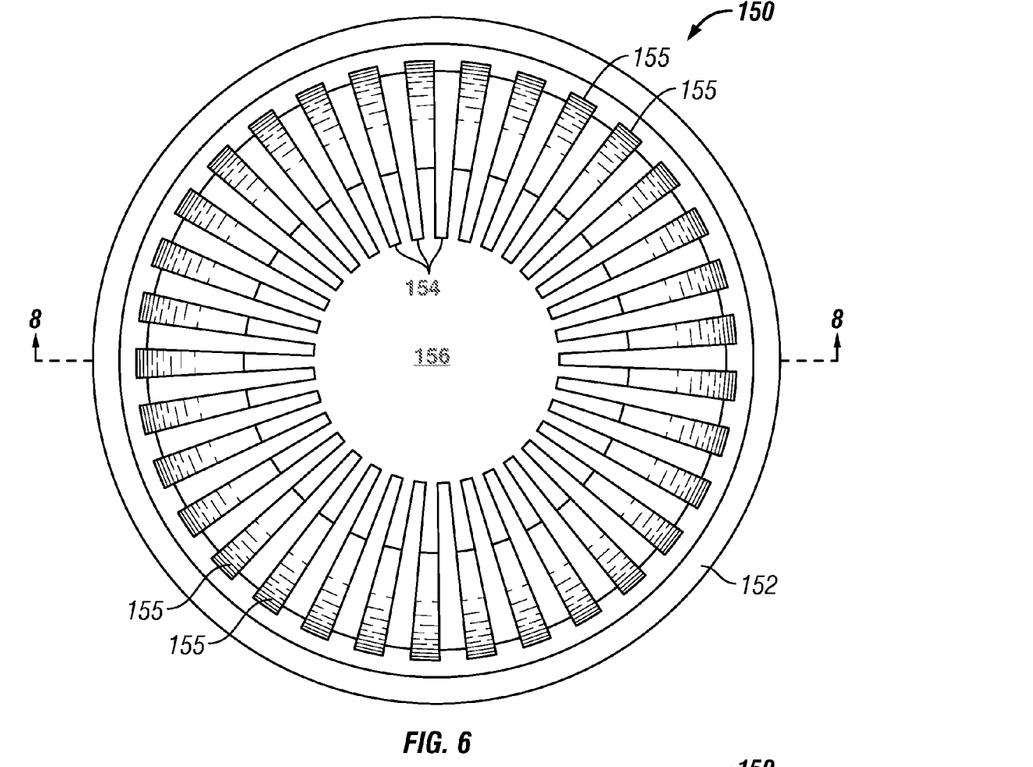
FIG. 6 is a plan view of the base of the piston assembly of FIG. 3.
Figure 7:
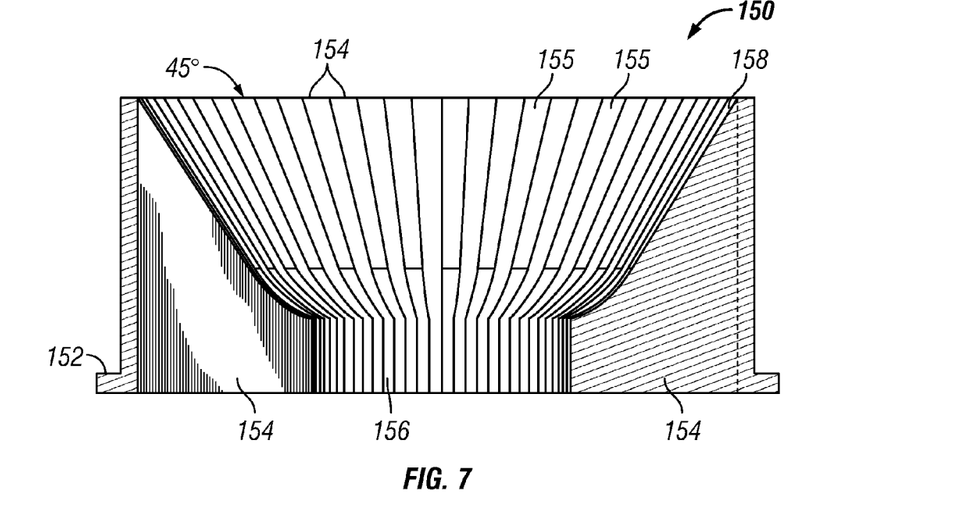
FIG. 7 is a sectional view of the base along line 8-8 of FIG. 6.

As shown in FIGS. 6 and 7, the base 150 includes a collar 152 and a plurality of ribs 154. The plurality of ribs 154 are integrally formed with collar 152 and extend radially inward to define a central passageway 156. The base 150 is constructed so as to (i) permit the hub 142 to be movably received by the central passageway 156 and (ii) allow the plurality of splines 144 to be movably interposed between the plurality of ribs 154 (see FIGS. 9 and 10). As shown in FIG. 7, the ribs 154 generally form a concave receiving surface 158 which inversely complements the convex supporting surface 147 of the piston 140. Accordingly, each rib 154 progresses from a full height at the collar 152 to a substantially lesser height at the perimeter of central passageway 156. In the preferred embodiment, the angular displacement of the receiving surface 158 is substantially 45 degrees. Further, the angular displacement of the supporting surface 147 of the piston 140 is substantially equivalent.

In the preferred embodiment, each spline 144 has a thickness substantially equal to that of each rib 154. Therefore, when the base 150 receives the piston 140 there exists limited and tightly controlled clearance between any rib-spline interface, thereby preventing the opportunity for the cassette material to become pinched or positioned between the elements during operation. The piston 140 may be manufactured from a lubricated material such as acetyl fluoropolymer (for example, Delrin AF from DuPont, Co., Wilmington, Del.), and the base 150 from a glass reinforced polycarbonate (for example, a 10% glass material Lexan 500 from GE Plastics, Pittsfield, Mass.), to permit largely unrestricted motion of the piston 140 relative to the base 150 despite the potential for repeated contact between two elements. The number of splines 144 and ribs 154 should be such that the space 145 between each spline 144 and the space 155 between each rib 154 (such being substantially equivalent if the thickness of each spline 144 is substantially equivalent to the thickness of each rib 154) is of such a distance to enable the adjacent splines (or ribs as the case may be) to support the cassette 120 across the spaces 145, 155.

The complementary shaping of the piston 140 and the base 150 enables a resting cassette pumping chamber 124, 126 to be supported by a constant surface area throughout an entire stroke of the piston 140, thereby foreclosing the opportunity for the cassette material to be stretched, unsupported or pinched during movement of the piston 140. Furthermore, the geometric relation between the elements permits a mathematical relation to be established. In the preferred embodiment, for example, the diameter of the piston 140 linearly decreases, relative to the interior of the pumping chamber, with the retraction of piston 140. A similar relation exists for the advancement of piston 140. Thus, during retraction of the piston 140, an enclosed volume is created which increases as a quadratic function of the piston's 140 movement. The relation can be used to maintain a constant fluid flow rate because the rate of piston movement can be controlled to achieve a predetermined flow rate.

Although the preferred embodiment defines a base 150 having a receiving surface 158 with a 45-degree angular displacement along the plurality of ribs 154, the angular displacement may measure from 30 to 60 degrees. Notwithstanding, the preferred embodiment ensures:
  (i) a relatively significant pumping chamber volume,
  (ii) full support of the cassette pumping chamber 124, 126 through an entire pumping stroke, and
  (iii) avoidance of trapped air within the pumping chamber 124, 126.

Figure 8:
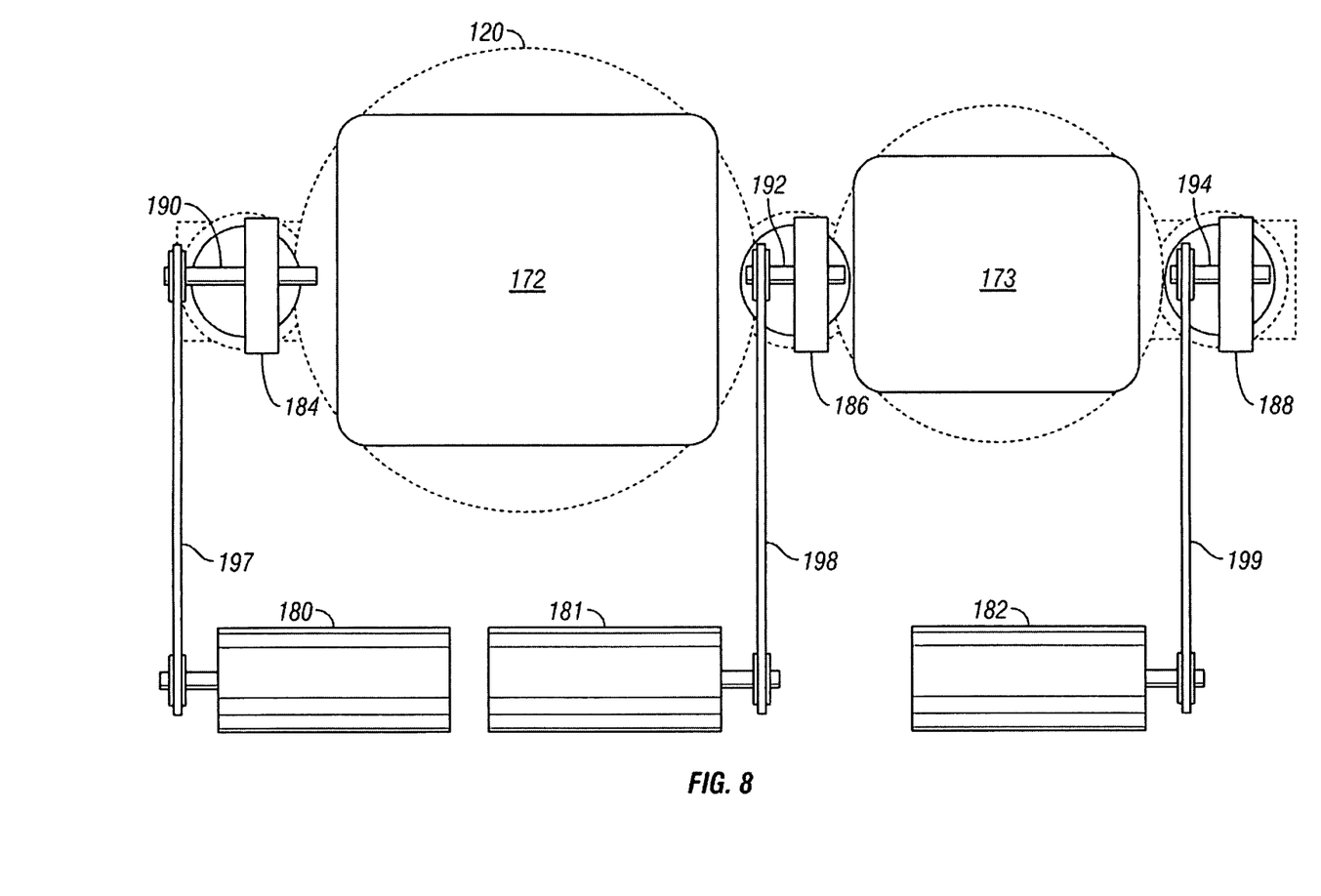
FIG. 8 is a view from beneath a pump mechanism which accommodates the disposable fluid cassette of FIG. 2.

FIG. 8 is a rear view of the elements of the pumping mechanism which accommodates the cassette 120 of FIG. 2 (an outline of the cassette 120 is provided). The pumping mechanism incorporates a pair of stepper motors, or pumping motors 172, 173. The pumping motors 172, 173 rotationally engage, through attached lead screws 143a, 143b, a threaded portion 141a, 141b of each piston 140a, 140b (see FIG. 1).

Three drive motors 180, 181, and 182 control the operation of the mechanism's valves. Drive motor 180 engages cam shaft 190 (driving inlet valves 184) through a timing belt 197. Drive motor 181 engages cam shaft 192 (driving inlet valves 186) through a timing belt 198. Drive motor 182 engages cam shaft 194 (driving outlet valve 188) through a timing belt 199.

Referring to both FIGS. 2 and 8, the interrelation of the pumping mechanism is better illustrated. The pumping mechanism, through the operation of a series of valves, controls the flow of fluid throughout the cassette 120. Specifically, a valve, if actuated, presses the first and second sheets of the cassette 120 together at a cassette valve location to occlude the valve location's corresponding flow path.

For the pumping mechanism, inlet valve 184 controls the introduction of fluid into the first pumping chamber 124. Inlet valve 186 controls the introduction of fluid into the second pumping chamber 126.

The inlet valves 184, 186 act on the cassette 120 at valve locations 134 and 136, respectively. Outlet valve 188 controls the flow of fluid from the second pumping chamber 126 by acting on cassette valve location 138.

As an example, in preparation of filling the first pumping chamber 124, valve 184 (at valve location 134) is de-actuated to permit fluid to flow into the chamber through fluid inflow path 123. Meanwhile, valves 186 and 188 (at valve locations 136 and 138, respectively) are actuated to close fluid paths 125 and 127, respectively. This permits the accumulation of fluid within the first pumping chamber 124.

Upon completion of the fill, valve 184 occludes flow path 123, and valve 186 is de-actuated to open fluid path 125, permitting fluid flow from the first pump chamber 124 to the second pump chamber 126. Upon completion of the fill for the second pump chamber 126, valve 186 is actuated to occlude fluid path 125, and valve 188 is de-actuated to open fluid outflow-path 127.

The first pump chamber 124 passively fills and then rapidly expels the collected fluid into the second chamber 126 at low pressure. The second chamber 126, once filled, expels the fluid downstream at high pressure, producing a pulsatile (cyclic) pressure profile downstream. Fluid movement, whether filling or being expelled from the pumping chambers 124, 126, is initiated through the movement of the mechanism's pump assemblies 110a, 110b.

Stroke volume for each pump chamber may be fixed or variable. The first pump chamber 124 is in the filling phase greater than 75% of the time and in the expulsion phase less than 25% of the time. These values may be shifted to extend the filling time and shorten the expulsion time depending on output needs or the fluid filling rate supplied by the patient to the first chamber.

The cross-sectional area of the first pump chamber 124 is larger than the second chamber 126 so that a shorter piston stroke may be used to pump a volume equivalent to the volume needed in the second chamber.

Referring back to FIG. 1 and the operation of the pump mechanism, a fastened retaining door 174 tightly constrains the cassette 120 against the upper surface of the pump mechanism. The retaining door 174 possesses a number of cavities 176a, 176b, the number corresponding to the number of pump assemblies included within the pump mechanism. The cavities 176a, 176b are complementary of and can fully receive at least a portion of the pistons 140a, 140b when they are in a fully advanced position. Accordingly, the conformance of the cavities 176a, 176b to the shaping of the pistons 140a, 140b enables the expulsion of substantially all the fluid from the pump chambers 124, 126 for a full piston stroke. Complete fluid displacement makes such pumping mechanism and its methodology suitable for single pumping stroke applications.

When the cassette 120 is operatively positioned in the pump mechanism, the cassette pumping chambers 124, 126 align with and rest upon the pump assemblies 110a, 110b. The retaining door 174 effectively constrains the cassette 120 during operation. The formed volume of the paths and chambers of the cassette 120 may be slightly greater or less than the nominal constraining volume defined by the rigid constituents of the pump mechanism. Practically, the firm restraints of the pump mechanism permit the development of relatively high fluid pressures within the cassette 120 without significant or detrimental deformation of the cassette material. Indeed, constraining the cassette 120 over effectively the entire cassette surface creates an inherently non-compliant system. Such non-compliance contributes to the ability of the pump mechanism to produce consistent, accurate volumetric fluid delivery.

In the preferred embodiment, the cassette pumping chambers 124, 126 do not rest directly upon the supporting surfaces of the piston 140 and/or base 150. Instead, a resilient material 178, attached about the upper portion of the base 150, operates to conform to the supporting surface of the piston assembly 110 without regard to whether the piston 140 is fully advanced, retracted or in some intermediate position. The resilient material 178 protects the pump mechanism from fluid intrusion in the event any liquid is spilled on the device operational environment. The resilient material 178 also acts to further protect the cassette 120 from damage that could inadvertently occur through the operation and movement of the piston assembly 110.

In an alternate embodiment, the resilient material 178 could include reinforcement means to provide additional rigidity to the resilient material 178. As an example, reinforcement means could include a fine metal mesh or cloth embedded within the material used to fabricate the resilient material 178. Alternatively, the resilient material 178 could include a spiral wire which is capable of concentric expansion to provide facial and lateral support for a resting cassette 120 about the interior of the base 150 (when piston 140 is in a retracted position) or about the piston 140 (when piston 140 is in an advanced position). Lastly, the material 178 could be formed of cloth altogether to eliminate any elasticity. This alternative embodiment, and its variations, could permit the use of fewer rib/splines or provide greater reliability in applications that require the piston assembly to operate in larger applications, in the presence of greater fluid pressures or both.

Figure 10:
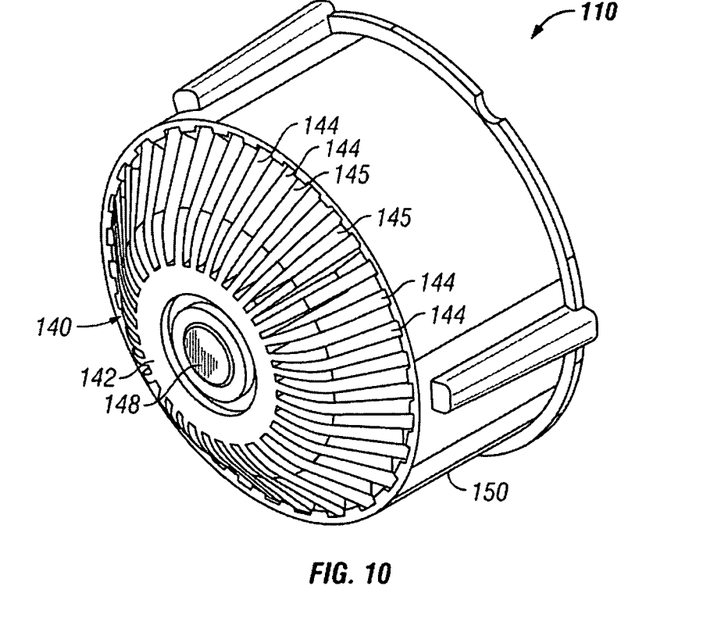
FIG. 10 is a perspective view of the piston assembly of FIG. 3 in a fully advanced state.

In FIG. 1 piston 140a is fully retracted (see also FIG. 9) and piston 140b is fully advanced (see also FIG. 10). Relative to fluid displacement, pump chamber 124 would be substantially full of fluid, and pump chamber 126 would have just expelled its contents. For the present embodiment, the pump mechanism can deliver substantially continuous fluid flow through the sequential filling and expulsion of fluid from the pumping chambers 124, 126.

Figure 11:
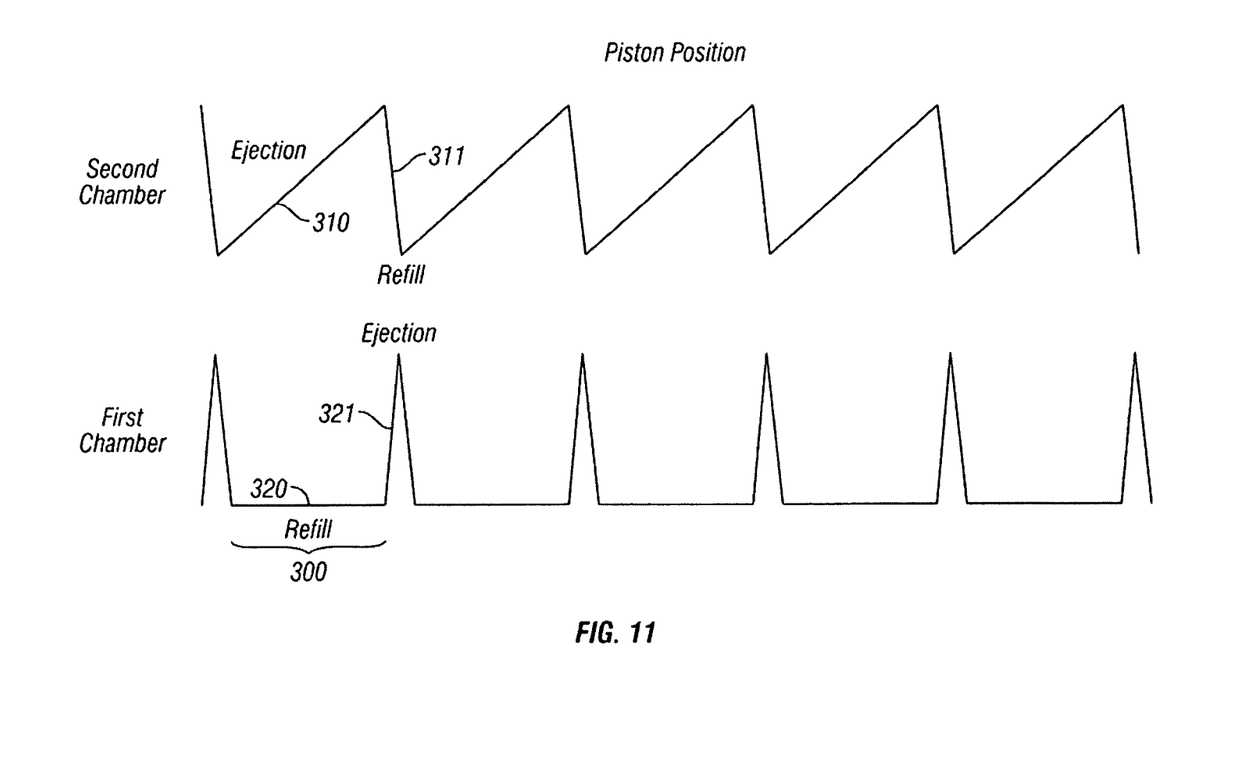
FIG. 11 is a timing diagram illustrating a cycle of the blood pump depicted in FIGS. 1-10 when operated in a pulsatile flow mode in accordance with a preferred embodiment of the present invention.

Turning now to FIG. 11, a timing diagram illustrating the operation of a preferred embodiment of the present invention in a pulsatile flow mode is depicted in accordance with a preferred embodiment of the invention. The timing diagram shows the piston positions for the first and second fluid chambers over the course of several pumping cycles.

In the preferred embodiment, because spline pistons are utilized, the flow rate of the fluid leaving the pumping chamber is related quadratically to the velocity of the piston. To achieve a pulsatile flow, the respective velocities of the pistons differ from each other during their refill and ejection cycles.

Period 300 represents one pumping cycle. Within each complete pumping cycle, each piston has a refill period and an ejection period. As can be seen in FIG. 11, the refill/ejection sequence is reversed between the pistons. In addition, the relative time spent in refill versus ejection is also reversed between the pistons. This is partly due to the differences in size between the fluid chambers.

When the first fluid chamber is in a refill period, the first piston 140a remains in a fully retracted position 320 as the chamber 124 passively fills. During this time, the second piston 140b is advancing gradually, ejecting fluid from the second chamber 126, as depicted by slope 310.

At the end of the refill period, the first piston 140a rapidly ejects fluid from the first chamber 124 at low pressure, as represented by slope 321. This rapid ejection from the first chamber is accommodated by a corresponding rapid retraction of the second piston 140b, producing a rapid refill period for the second fluid chamber 126, represented by slope 311.

Though fluid ejection from the second chamber is slower than the first chamber, it occurs at higher pressure. The higher fluid pressure produced by the second chamber ejection produces the pulsatile flow downstream.

An operator may specify a particular frequency, corresponding to a simulated heart rate, at which the operator wishes the pulsatile flow to run. In order to simulate normal physiological conditions, a frequency of between 50-90 beats per minute is typically used.

As explained above, in the preferred embodiment of the present invention, the spline piston included a contact pressure sensor that permits monitoring of fluid pressure within a pumping chamber associated with the piston. As the piston engages the constrained, flexible cassette containing blood and/or other fluids, the pressure sensor is used to assess whether an adequate input volume was received in order to maintain a user specified output flow rate. If inadequate input volume is received into the first chamber, the operator is notified of the problem and has the option to correct the limitation or reduce the output flow rate.

Figure 12:
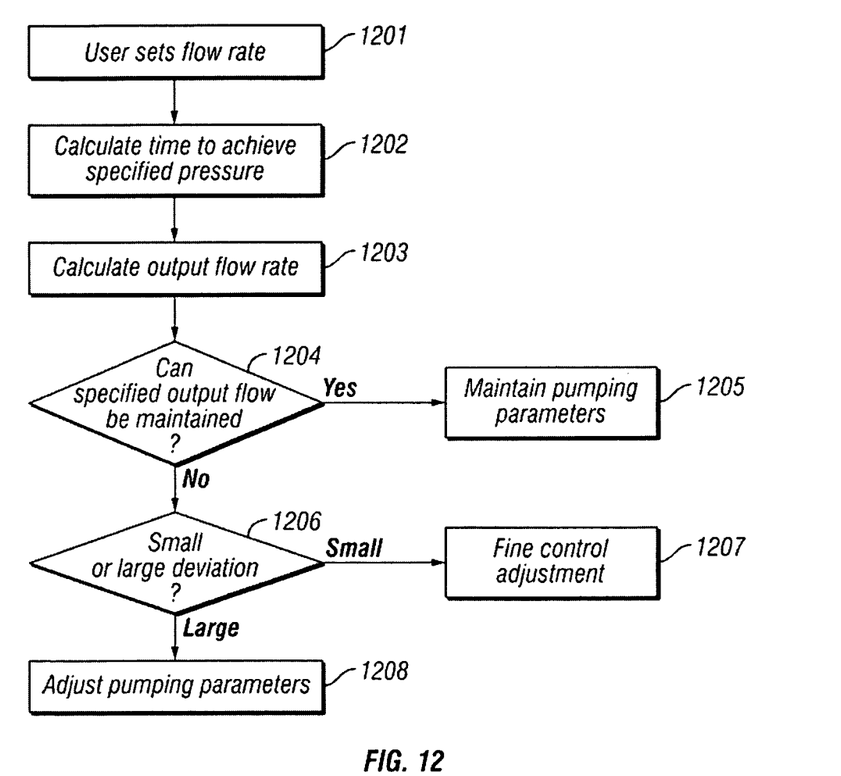
FIG. 12 is a flowchart illustrating the process of adapting output flow rate in accordance with a preferred embodiment of the present invention.

FIG. 12 is a flowchart illustrating the process of adapting output flow rate in accordance with a preferred embodiment of the present invention. The invention utilizes the pressure sensor information from the pistons and adapts the output flow rate to match the input flow rate.

A user initially sets the desired flow rate for the pump (step 1201). At the end of each pump cycle, a microprocessor calculates the time taken to achieve a specified pressure at the end of the refill period (step 1202). This data is then used to calculate the output flow rate (step 1203).

The microprocessor compares the output flow rate of the previous pump cycle to a pre-set value range to determine if the specified output flow can be maintained (step 1204). If so, the pump parameters are maintained at their current levels (step 1205).

If the specified output flow cannot be maintained, the microprocessor then determines if the output flow rate of the previous pump cycle has made a small or large deviation from the specified target (step 1206). For example, a small deviation may be defined as an output flow within ±10% of the specified output flow rate, which would require only slight adjustments to the pumping parameters. In this same example, any deviation greater than ±10% of the specified output flow rate would be considered a large deviation.

If the deviation from the specified output flow rate is small, the microprocessor instructs the piston pump motor to make fine control adjustments to its flow rate relative to available input (step 1207). Fluid output rate can be adjusted either by increasing or decreasing piston velocity (stroke rate), by changing stroke volume, or a combination of the two methods.

If the deviation from the specified output flow rate is large, the microprocessor instructs the piston motor pump to make large increment adjustments to its flow rate relative to available input (step 1208). Large increment adjustments are needed to bring the output flow close to the specified rate in as little time as possible to minimize the time during which large deviations occur. In such situations, fine control adjustments would be unable to bring the output flow rate closer in line with the specified rate within the necessary time frame (the next pump cycle).

For example, if the output flow rate of the previous pump cycle deviated from the specified rate by 40% (e.g., the output flow was only 60% of what it should have been), the microprocessor will instruct the pump to make a large increment adjustment to the pumping parameters in an attempt to get the output flow rate closer to the target rate on the next pump cycle. Several large increment adjustments may be needed before the microprocessor switches to fine control. Using the same example above, the first adjustment might bring the output flow rate from 60% to 80% of the target rate and a second large increment adjustment might bring the output flow from 80% to 90+%. From that point, the microprocessor can switch back to fine control.

The microprocessor adjusts the output flow rate for each pump cycle.

The range of flow rates fall within operator-set constraints such that the operator is notified in the event the input flow cannot support the minimum output flow rate, or conversely, if the input rate supports a flow rate above the specified maximum output flow rate.

Figure 13:
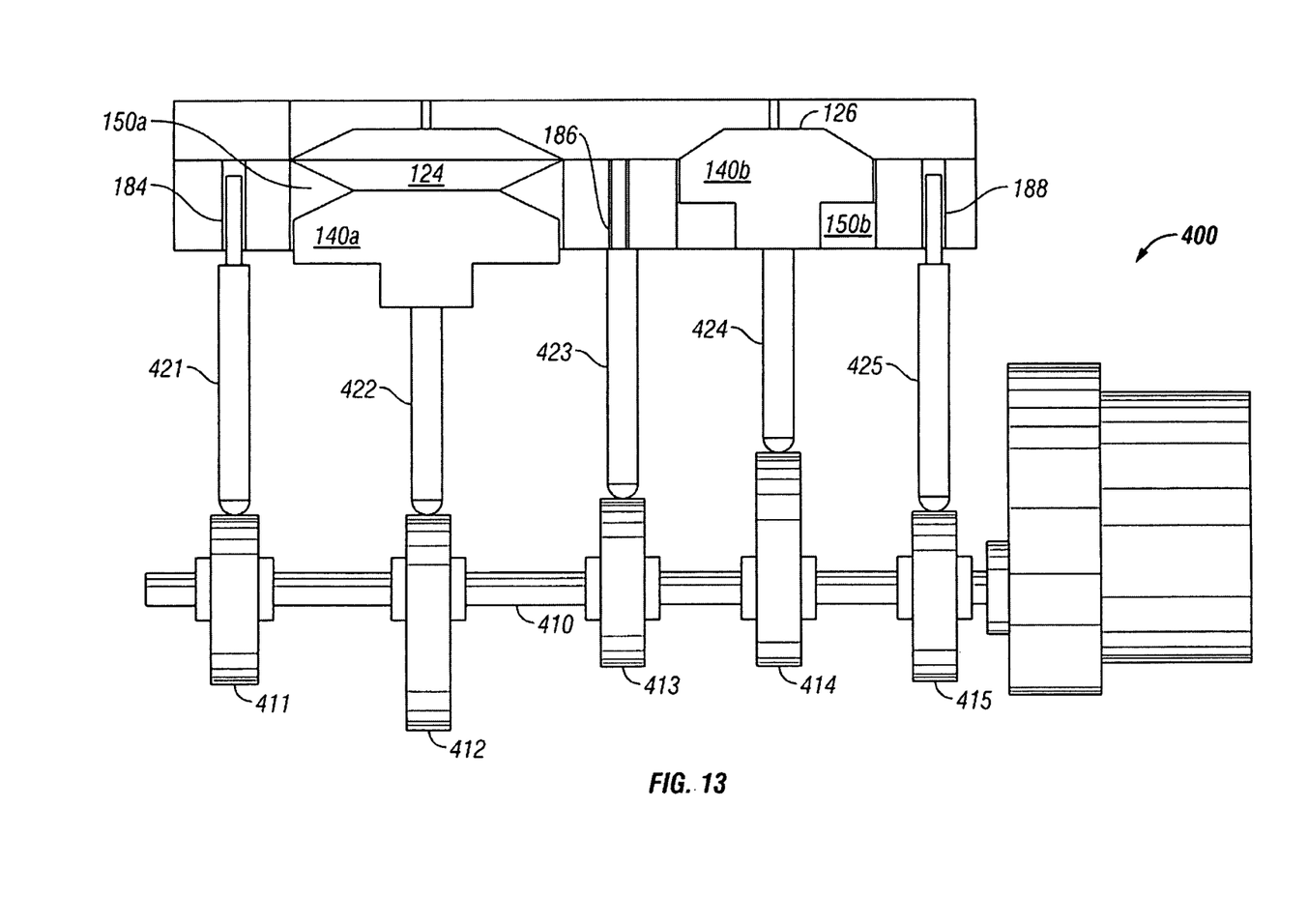
FIG. 13 shows an alternate embodiment of the present invention in which the fluid pump is driven by a single motor, using cams.

FIG. 13 shows an alternate embodiment of the present invention in which the fluid pump is driven by a single motor, using cams. In this embodiment, the dual pumping motors 172, 173 and valve control motors 180-182 are replaced with a single drive motor 400.

Motor 400 drives cam shaft 410 with attached cams 411-415. Cam 412 drives the first piston 124 through cam follower rod 422, and cam 414 drives the second piston 126 by means of cam follower rod 424. The lower ends of rods 422, 424 are rounded to ride upon the surface of cams, and the upper ends of rods are threaded for connection to the pistons.

Cam 411 drives the first valve 184 through cam follower rod 421, which has its lower end rounded to ride on cam 411. The second valve 186 is driven by cam 413 through cam follower rod 423, and the third valve 188 is driven by cam 415 through rod 425.

Like the other embodiments described above, the output flow rate of the embodiment depicted in FIG. 13 can be adjusted via microprocessor control.

An alternate operation of the present invention allows for the production of continuous fluid flow instead of pulsatile flow. This is accomplished by changing the timing of the piston and valve operations.

The continuous flow operation begins with the first valve 184 opening while piston 140a retracts, drawing fluid into the first chamber 124. At the same time that the first chamber 124 is filling, valve 186 is closed and valve 188 is opened as the second piston 140b moves upward, pumping fluid from second chamber 126 to the patient.

When the first piston 140a reaches its lowermost position and the second piston 140b approaches its uppermost position, valve 184 is closed, and second valve 186 is opened to permit fluid flow from the first chamber 124 to the second chamber 126.

The first piston 140a then begins to move upward while second piston 140b moves downward, resulting in fluid being pumped from the first chamber 124 into the second chamber 126. Unlike during pulsatile flow operation, the third valve 188 is kept open as fluid is being pumped from the first to second chamber. In addition, the downward movement of the second piston 140a is slower than the upward movement of the first piston 140a. As a result, some of the fluid being pumped from first chamber 124 into the second chamber 126 is also pumped out through outlet path 127 to the patient. By operating the pistons and valves in this manner, fluid is continuously being pumped through the outlet path 127 regardless of which piston is moving up or down.

The rate of travel of pistons 140a, 140b are selected so that the amount of fluid being pumped out through outlet path 127 is essentially the same when the fluid is being pumped from first chamber 124 as it is when the fluid is being pumped from second chamber 126.

When the first piston 140a reaches the top position and second piston 140b reaches the bottom position, the next cycle is ready to begin.

One embodiment of the present invention enables the sterile cassette to be refilled with a second fluid as a means to increase the circulating volume and thereby increase the pressure in the patient, increasing the flow rate returning from the patient to the pump.

The present invention can be constructed in single-pump or multiple-pump configurations.

The adaptive piston-pump of the present invention prevents excessive negative pressures in the pump inlet conduit and the patient's venous system. If further coupled with a second fluid input capability, the invention can infuse the specific fluid volumes for supporting an output flow rate that maintains a patient's arterial blood pressure within a prescribe range.

Figure 14:
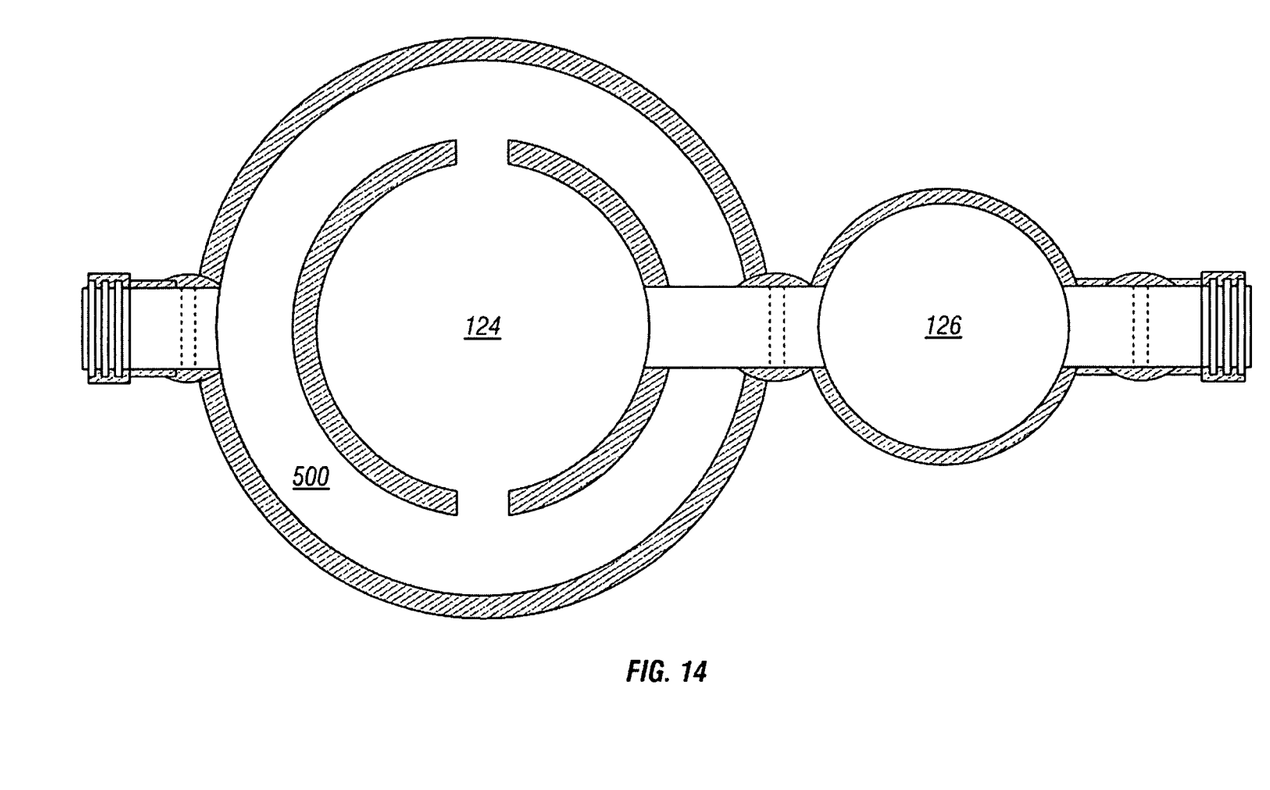
FIG. 14 shows an alternate fluid cassette in which the first pump chamber is incorporated into a fluid reservoir.

FIG. 14 shows an alternate fluid cassette in which the first pump chamber is incorporated into a fluid reservoir. In the application of an extracorporeal circuit, the patient blood flows by gravity siphon into a reservoir. In the alternate embodiment of the present invention, instead of connecting tubing as a conduit between the reservoir and the first chamber, the first chamber 124 is incorporated into a section of the reservoir 500. Making the pump cassette would be an integral component to the reservoir.

In addition to applications such as Extracorporeal Membrane Oxygenator (ECMO), the present invention may be employed as an artificial heart or cardiac assist device. The stroke volume and stroke rate are adaptive based on the available input rate. This functionality is comparable to that of a human heart. A heart essentially pumps what it receives. The venous vessels are highly compliant reservoirs. Sitting at rest, the veins are full. Upon commencement of physical activity or chemical stimulation, muscles contract, squeezing the blood reservoir, which pumps the blood toward the right atrium of the heart. The atrium fills faster to accept the increased volume and contracts to deliver the volume to the right ventricle, which in turn fills faster and contracts earlier to expel the increased volume to the lungs. The heart rate and stroke volume increases to accommodate the increased input rate. In similar fashion, the piston pump of the present invention can adapt its stroke volume and stroke rate based on available input rate and volume, closely simulating the variable functionality of a heart.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated. It will be understood by one of ordinary skill in the art that numerous variations will be possible to the disclosed embodiments without going outside the scope of the invention as disclosed in the claims.

I claim:
1. A fluid pump system comprising:
(a) a cassette comprising a first pump chamber and a second pump chamber;
(b) a first piston proximal to said first pump chamber;
(c) a second piston proximal to said second pump chamber;
(d) a first valve proximal to said first pump chamber;
(e) a second valve located between said first pump chamber and said second pump chamber;
(f) a third valve proximal to said second pump chamber;
(g) a control system configured to control the operation of said pistons and said valves; and
(h) wherein
said first pump chamber and said second pump chamber are in liquid communication with each other;
said first pump chamber is larger than said second pump chamber;
said cassette is formed by two flexible sheets;
said cassette is incorporated into a section of a fluid reservoir such that said cassette is integral to said fluid reservoir;
said first piston and a first base portion of said first pumping chamber are configured in complementary shapes to enable said first pump chamber when resting to be supported by a constant surface area throughout the stroke of said first piston;
said second piston and a second base portion of said second pumping chamber are configured in complementary shapes to enable said second pump chamber to be supported by a constant surface area throughout the stroke of said second piston;
said first pumping chamber interfaces with the supporting surfaces of said first piston via a resilient material attached about said first base portion and operates to conform to the supporting surface of said first piston without regard to whether said first piston is fully advanced, retracted or in some intermediate position;
said second pumping chamber interfaces with the supporting surfaces of said second piston via a resilient material attached about said second base portion and operates to conform to the supporting surface of said second piston without regard to whether said second piston is fully advanced, retracted or in some intermediate position;
said first piston causes liquid to flow from said first pump chamber to said second pump chamber when said first piston is advanced;
said second piston causes fluid to flow from said second pump chamber to a biological destination when said second piston is advanced;
said first valve occludes fluid flow into and out of said first pump chamber when said first piston is advancing, and allows fluid flow from a biological source into said first pump chamber when said first piston is retracting;
said second valve occludes fluid flow between said first pump chamber and said second pump chamber when said first piston is retracting and when said second piston is advancing;
said second valve allows fluid flow from said first pump chamber into said second pump chamber when said first piston is advancing;

said third valve occludes fluid flow into and out of said second pump chamber when said second piston is retracting;

said third valve allows fluid flow out of said second pump chamber to said biological destination when said second piston is advancing;

said first valve is controlled by a first cam shaft that is mechanically coupled to a first drive motor via a first timing belt;

said second valve is controlled by a second cam shaft that is mechanically coupled to a second drive motor via a second timing belt;

said third valve is controlled by a third cam shaft that is mechanically coupled to a third drive motor via a third timing belt;

said control system is configured to activate said pistons to be advanced according to a time-varying velocity profile;

said control system is configured to achieve pulsatile flow from the output of said second pump chamber by controlling the relative velocities of said pistons during the refill and ejection cycles of said pistons;

said control system is configured to maintain a steady discharge rate from said second pump chamber by adjusting the velocity of said pistons and/or by changing the stroke volume of said pistons;

said control system is configured to passively fill said first pump chamber during the time fluid is expelled from said second pump chamber;

said control system is configured to rapidly expel collected fluid from said first pump chamber into said second pump chamber at low pressure; and said control system is configured to expel fluid from said second pump chamber at high pressure.

2. The fluid pump system of claim 1, wherein said two flexible sheets are bonded together along a selected bond area to form particularized open flow paths and chambers.

3. The fluid pump system of claim 2, wherein said flexible sheets are made of polyvinylchloride.

4. The fluid pump system of claim 1, wherein said first piston and said second piston are spline pistons.

5. The fluid pump system of claim 1, further comprising:
a first pressure sensor incorporated into said first piston; and
a second pressure sensor incorporated into said second piston;
wherein said first pressure sensor and said second pressure sensor permit monitoring of fluid pressure within said first pump chamber and said second pump chamber.

6. The fluid system of claim 5, wherein said control system in part (g) can adjust the operation of said pistons and said valves in response to fluid pressure data from said pressure sensors.

7. The fluid system of claim 1, wherein said control system in part (g):
adjusts output flow from said fluid pump in large percentage increments if the output flow rate deviates outside a pre-determined value range; and
adjusts output flow from said fluid pump in fine percentage increments if the output flow rate is within a pre-determined value range.

8. The fluid pump system of claim 1, wherein said pistons are driven by separate stepper motors.

9. The fluid pump system of claim 1, wherein said control system can also produce a continuous fluid outflow by keeping said third valve open when said first piston is advancing and said second piston is retracting, wherein said second piston retracts slower than the advancement of said first piston.

* * * * *